United States Patent [19]
Ron et al.

[11] Patent Number: 5,651,979
[45] Date of Patent: Jul. 29, 1997

[54] APPARATUS AND METHOD FOR DELIVERING A BIOLOGICALLY ACTIVE COMPOUND INTO A BIOLOGICAL ENVIRONMENT

[75] Inventors: Eyal S. Ron, Lexington; Matthew E. Schiller, Waltham; Eric Roos, Grafton, all of Mass.

[73] Assignee: Gel Sciences, Inc., Bedford, Mass.

[21] Appl. No.: 473,218

[22] Filed: Jun. 7, 1995

Related U.S. Application Data

[63] Continuation-in-part of Ser. No. 413,409, Mar. 30, 1995.
[51] Int. Cl.$^6$ ............................ A61F 2/02; A61K 9/22
[52] U.S. Cl. .................... 424/423; 604/892.1; 604/891.1
[58] Field of Search ........................ 604/892.1, 891.1; 424/423

[56] References Cited

U.S. PATENT DOCUMENTS

| | | |
|---|---|---|
| 3,604,417 | 9/1971 | Stolzenberg et al. . |
| 3,845,770 | 11/1974 | Theeuwes et al. . |
| 4,474,575 | 10/1984 | Eckenhoff et al. . |
| 4,539,004 | 9/1985 | Eckenhoff et al. . |
| 4,678,467 | 7/1987 | Eckenhoff et al. . |
| 4,716,031 | 12/1987 | Eckenhoff et al. . |
| 4,777,049 | 10/1988 | Magruder et al. . |
| 4,800,056 | 1/1989 | Eckenhoff et al. . |
| 4,814,180 | 3/1989 | Eckenhoff et al. . |
| 5,082,668 | 1/1992 | Wong et al. . |
| 5,147,654 | 9/1992 | Place et al. . |
| 5,312,390 | 5/1994 | Wong . |
| 5,413,572 | 5/1995 | Wong et al. . |

*Primary Examiner*—Carlos Azpuru
*Attorney, Agent, or Firm*—Choate, Hall & Stewart

[57] ABSTRACT

System for delivery of a biologically active substance into an environment. First and second chambers are separated by a moveable partition. The first chamber includes a polymer gel network which undergoes a volume change in response to an environmental condition such as pH. The first compartment includes a screen or membrane for confining the polymer gel network while allowing communication with fluid in an environment. The second compartment contains a biologically active compound or drug which is delivered to the environment through an orifice in the second compartment. Upon the occurrence of the triggering environmental condition, the polymer gel network undergoes a volume change which moves the moveable partition expelling the drug through the orifice. Drug delivery is initiated and continues only when the appropriate environmental condition or trigger is met.

12 Claims, 3 Drawing Sheets

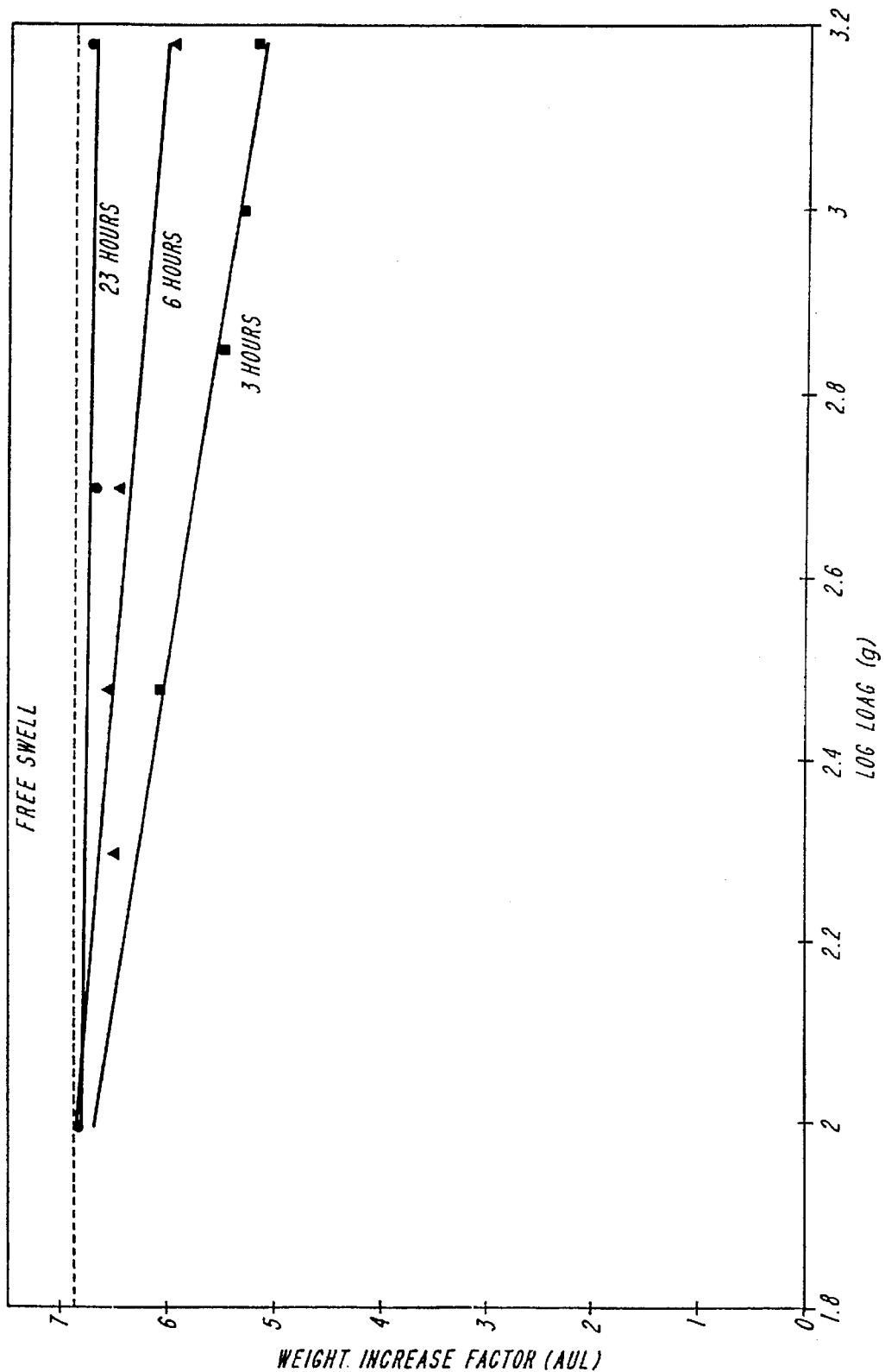

APPARATUS AND METHOD FOR DELIVERING A BIOLOGICALLY ACTIVE COMPOUND INTO A BIOLOGICAL ENVIRONMENT

This application is a continuation-in-part of co-pending application 08/413,409 filed Mar. 30, 1995, the entire contents of which are incorporated herein by reference.

BACKGROUND OF THE INVENTION

This invention relates to method and apparatus for delivering a biologically active compound to a biological environment in a controlled fashion.

The more precise control of the release of orally administered drugs has long been sought. In particular, it is desired that an orally administered drug or other biologically active compound be released only upon the occurrence of a desired environmental condition within a biological system. For example, it may be desired that a biologically active compound be released only in the intestines rather than being released as the material passes through the mouth and stomach. Prior art controlled release techniques typically result in initiation and/or continuation of controlled release as a function of time after ingestion.

An example of a controlled release oral delivery system is the so-called osmotically-controlled delivery system. See, for example, Wong et al., U.S. Pat. No. 5,413,572; Theeuwes et al., U.S. Pat. No. 3,845,770; Wong, U.S. Pat. No. 5,312,390; Eckenhoff et al., U.S. Pat. No. 4,474,575; Place et al., U.S. Pat. No. 5,147,654; Eckenhoff et al., U.S. Pat. No. 4,539,004; and Magruder et al., U.S. Pat. No. 4,777,049. The technology disclosed in these patents utilizes the osmotic pressure resulting from concentration gradients to expel a biologically active substance into the body. In some embodiments, the osmotic pressure moves a moveable partition to effect drug release. Wong et al., in the '572 patent, also teaches the use of a hydrogel which expands when contacted with water, the expansion serving to expel the biologically active material.

Osmotic pressure based systems have the shortcoming that they depend on flux and pressure for their operation. It is known that a desirable drug delivery system should be independent of both flux and pressure. In addition, an osmotic pressure based system has release kinetics that are highly dependent on orifice size. The osmotic pumps of the prior art operate on the principle of net flux of water across a semipermeable membrane into a compartment that contains the osmotic driving agent. The rate of flux is controlled by the water permeable membrane characteristics and the difference in osmotic and hydrostatic pressure between the compartment containing the osmotic driving agent and the outside of the device. The flux J of water may be represented as $J = K \cdot A (\sigma \Delta \pi - \Delta P)$ where K is the permeability of the membrane, A is the membrane's surface area, $\sigma$ is the osmotic coefficient of the membrane, $\Delta \pi$ is the osmotic pressure and $\Delta P$ is the hydrostatic pressure. See, Theeuwes et al., "Principles of the Design and Operation of Generic Osmotic Pumps for the Delivery of Semisolid or Liquid Drug Formulations," *Annals of Biomed. Eng.*, 4(343), 1976.

As stated above, the prior art osmotic systems are also very sensitive to the size of the delivery orifice. See, Theeuwes et al., "Elementary Osmotic Pump," *J. Pharm. Sci.*, 64(1987), 1975. The orifice size must be small so as to minimize diffusion through the orifice and yet still be sufficiently large to minimize hydrostatic pressure inside the system that would affect the zero-order release kinetics. Further, the release kinetics in osmotic systems are independent of pH and motility of the gastrointestinal tract. See, Fara et al., "Osmotic Pumps in Drug Delivery Devices—Fundamentals and Applications," Praveen Tyle, ed., Marcel Dekker, Inc., p137 (New York).

Other systems for non-continuous delivery of drugs, for example, the Pulsncap system are known in the prior art. In this system there is a limiting osmotic pressure which, when achieved, pushes out a cap to begin drug release.

Reference is also made to the prior art connection of an osmotic system to a syringe-like system to provide an external continuous IV/IM/SQ infusion. See, U.S. Pat. No. 3,604,417 and Urquhart et al., "Rate-Controlled Delivery Systems in Drug and Hormone Research," *Ann. Rev. Pharmacol. Toxicol.*, 24(199), 1984.

In none of the prior art delivery systems is there initiation and continuation of release upon the occurrence of an environmental condition such as pH which changes from place to place within the body.

As discussed in co-pending application Ser. No. 08/413,409 of which this application is a continuation-in-part, volumetric change phenomena have been observed in three-dimensional, permanently crosslinked polymer gel networks. As an external environmental condition (e.g., temperature, solvent composition, pH, electric field, light intensity and wavelength, pressure, ionic strength, osmolarity) is changed, the polymer gel network contracts and/or expands in volume. The volume of such a gel may, under certain circumstances, change reversibly by a factor as large as several hundred when the gel is presented with a particular external condition (i.e., the gel is a "responsive" gel; see, for example, Tanaka *Phys. Rev. Lett.* 40(820), 1978; Tanaka et al., *Phys. Rev. Lett.* 38(771), 1977; Tanaka et al., *Phys. Rev. Lett.* 45(1636), 1980; Ilavsky, *Macromolec.* 15(782), 1982; Hrouz et al., *Europ. Polym. J.* 17, p361, 1981; Ohmine et al., *J. Chem. Phys.* 8(6379), 1984; Tanaka et al., *Science* 218(462), 1982; Ilavsky et al., *Polymer Bull.* 7(107), 1982; Gehrke "Responsive Gels: Volume Transitions II", Dusek (ed.), Springer-Verlag, New York, p81–144, 1993; Li et al., *Ann. Rev. Mat. Sci.* 22(243), 1992; and Galaev et al., *Enzyme Microb. Technol.* 15(354), 1993, each of which is incorporated herein by reference).

As disclosed in the co-pending application Ser. No. 08/413,409 referred to above, a number of significant studies have demonstrated the potential of responsive gels in solutes/solvent separations (see, for example, Kussler, U.S. Pat. No. 4,555,344) and in biomedical applications (see, for example, Hoffman, U.S. Pat. No. 4,912,032). Synthesis of a gel may utilize monomers and/or polymers whose toxicologic hazard characteristics are ill defined (e.g., n-isopropylacrylamide, NIPA and related acrylic monomers, polymers and copolymers). Further, synthesis of a gel may use crosslinkers known to be toxic (e.g., divinylsulfone (DVS), glutaraldehyde, divinylbenzene, n-n-methylenebisacrylamide, and the like). Harsh and Gehrke (*J. Control. Rel.* 17(175), 1991, incorporated herein by reference) have created certain gels based on cellulose ether polymeric precursor materials. These cellulosic ether precursor materials are currently acceptable by the U.S. Food and Drug Administration, but these gels were made using toxic DVS crosslinkers that are not FDA acceptable. One way to avoid use of toxic chemical crosslinkers is by use of radiation crosslinking. This method is problematic inasmuch as it may lead to the presence of unreacted monomers.

As disclosed in the co-pending application Ser. No. 08/413,409, a suitable gel material for use in a biological environment is a crosslinked, responsive polymer gel network comprising polymer chains interconnected by way of multifunctional crosslinkers. The polymer chains and crosslinkers have a known acceptable toxicological profile, hereinafter referred to as "KATP." Another suitable material is a crosslinked, responsive polymer gel network comprising polymer chains interconnected by way of KATP crosslinkages. A further suitable material is a crosslinked, responsive polymer gel network having polymer chains interconnected by way of a crosslinker in which each of the polymer crosslinkers is obtainable from a precursor that is used in a process for making material that has a KATP. These gels have the characteristic that, when leached, the leachate from the network also has a KATP as well as any residual elements in the network. The gel solvent may also have a KATP.

SUMMARY OF THE INVENTION

The apparatus according to one aspect of the invention for controlled delivery of a biologically active compound to a biological environment includes first and second compartments separated by a moveable partition. The first compartment includes a screen or membrane forming at least a portion of a side of the first compartment. The first compartment contains a polymer gel network which undergoes a volume change in response to an environmental condition which may vary in the biological environment or which may be external to the environment. The second compartment contains an effective amount of a biologically active compound and includes an orifice communicating with the biological environment. When a preselected condition is encountered, the volume of the polymer gel network changes, causing the moveable partition to move to discharge the biologically active compound into the biological environment through the orifice. In a preferred embodiment, the selected environmental condition is pH. Other environmental triggers are temperature, electric fields, magnetic fields, electromagnetic radiation, light intensity and wavelength, pressure, ionic strength, solvent and osmolarity. It is preferred that the polymer gel network has a known acceptable toxicological profile (KATP). Preferred responsive polymer gel network materials include polysaccharide chains crosslinked with a multifunctional carboxylic add obtainable from an acyl halide derivative of the acid. The preferred polymer chains are polysaccharides (e.g., starch or cellulose ethers) and the preferred multifunctional carboxylic acid is selected from the group consisting of adipic acid, sebacic acid, succinic acid, citric acid, 1, 2, 3, 4-butanetetracarboxylic acid, and 1, 10 decanedicarboxylic acid. Particularly preferred polymers are cellulose ethers selected from the group consisting of hydroxyethylcellulose, hydroxypropylcellulose, and hydroxypropylmethylcellulose. It is preferred that the gel exhibit substantially pressure independent volume changes at hydrostatic pressures in the range of 0.30–1.3 atmospheres.

The responsive polymer gel networks suitable for use in the apparatus of the invention may be responsive to any of a variety of triggers some of which have been set forth above. In particular, the pH-response may be triggered by a change in an environmental condition to which the gel is exposed, such as a change in ion concentration, solvent concentration, electric field, magnetic field, electromagnetic radiation, or mechanical force.

Methods for making crosslinked polymer networks include selecting a polymeric staging material capable of being crosslinked, wherein the polymeric starting material selected for the particular use has a known acceptable toxicological profile for the particular use or for a related use; selecting a crosslinker capable of crosslinking the polymeric starting material, wherein the crosslinker selected for the particular use has a known acceptable toxicological profile for the particular use or for a related use; and contacting the crosslinker and polymeric starting material under conditions sufficient to form the three-dimensional, crosslinked polymer network.

Another method involves selecting a crosslinker capable of crosslinking the polymeric starting material, so that the resulting network, after formation, contains a crosslinkage that has a known acceptable toxicological profile. Preferred methods include the steps of contacting a crosslinker comprising an acyl halide derivative of a multifunctional carboxylic acid with a polysaccharide under conditions sufficient for the three-dimensional, polymer gel network to form so that the gel network includes polysaccharide chains crosslinked with the acid. Particularly preferred methods use a polysaccharide selected from the group consisting of starch and cellulose ethers, which group includes, for example, hydroxyethylcellulose, hydroxypropylcellulose, hydroxypropylmethylcellulose, and modified food starch.

Preferred methods use a crosslinker that is an acyl halide derivative of a multifunctional carboxylic acid, such as, for example, an acyl halide derivative of adipic acid, sebacic acid, succinic acid, 1,2,3,4-butanetetracarboxylic acid, or 1,10 decanedicarboxylic acid. Other preferred methods use bifunctional crosslinkers such as, for example, divinylsulfone. Still other preferred methods utilize irradiation energy as a crosslinker.

The apparatus and system of the invention is thus a chemo-mechanical system in which the driving force is provided by the non-continuous expansion properties of the hydrogel. The hydrogels of the invention expand at a rate independent of water influx. The hydrogels of the invention may be submerged in water or other liquid and either remain collapsed or swell at their own rate but only upon the appropriate trigger. The delivery system of the invention can also be designed to cycle on and off. By first applying and then removing the trigger, the system would release the drug or stop the release by design and in a controlled fashion. The system of the present invention is also, within limits, independent of the hydrostatic pressure of the fluid in which the device is placed.

BRIEF DESCRIPTION OF THE DRAWING

FIG. 4 is a graph of hydrogel weight increase factor versus hydrostatic pressure (log load).

DESCRIPTION OF THE PREFERRED EMBODIMENT

Figure 1:
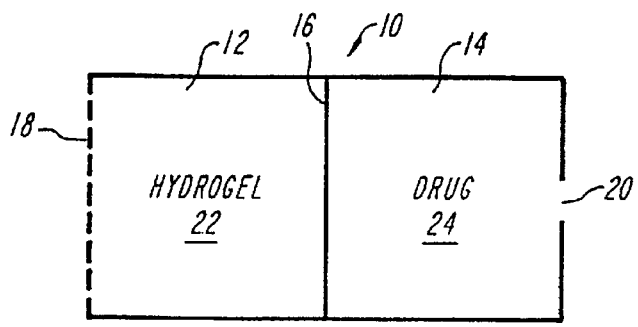
FIG. 1 is a cross-sectional view of an embodiment of the invention disclosed herein.

With reference to FIG. 1, a controlled drug delivery device 10 includes a first compartment 12 separated from a second compartment 14 by a moveable partition 16. The first compartment 12 includes a side having a screen or membrane 18. The second compartment 14 includes an orifice 20. First compartment 12 contains hydrogel 22 and the second compartment 14 contains a biologically active material or drug 24. The screen or membrane 18 retains the hydrogel 22 within the compartment 12 but allows communication with fluids in a biological environment (not shown) into which the device 10 is placed. The screen or membranae 18 may be a semipermeable membrane if desired.

As will be discussed in more detail hereinbelow, the hydrogel 22 is selected to undergo a volume change such as an expansion in response to the occurrence of an environmental condition such as pH. Upon occurrence of such a condition, the hydrogel 22 will expand, thereby moving the moveable partition 16 to the right in FIG. 1. This movement will decrease the volume in the second compartment 14, causing the biologically active material 24 to exit through the orifice 20 into a biological environment (not shown).

The drug delivery device 10 is made of any suitable, biologically inert material, such as polyethylene, polypropylene and polyurethane. A preferred screen or membrane 18 is cellulose acetate. The biologically active material or drug 24 may be any material approved for use in a particular diagnostic or treatment protocol.

Figure 2:
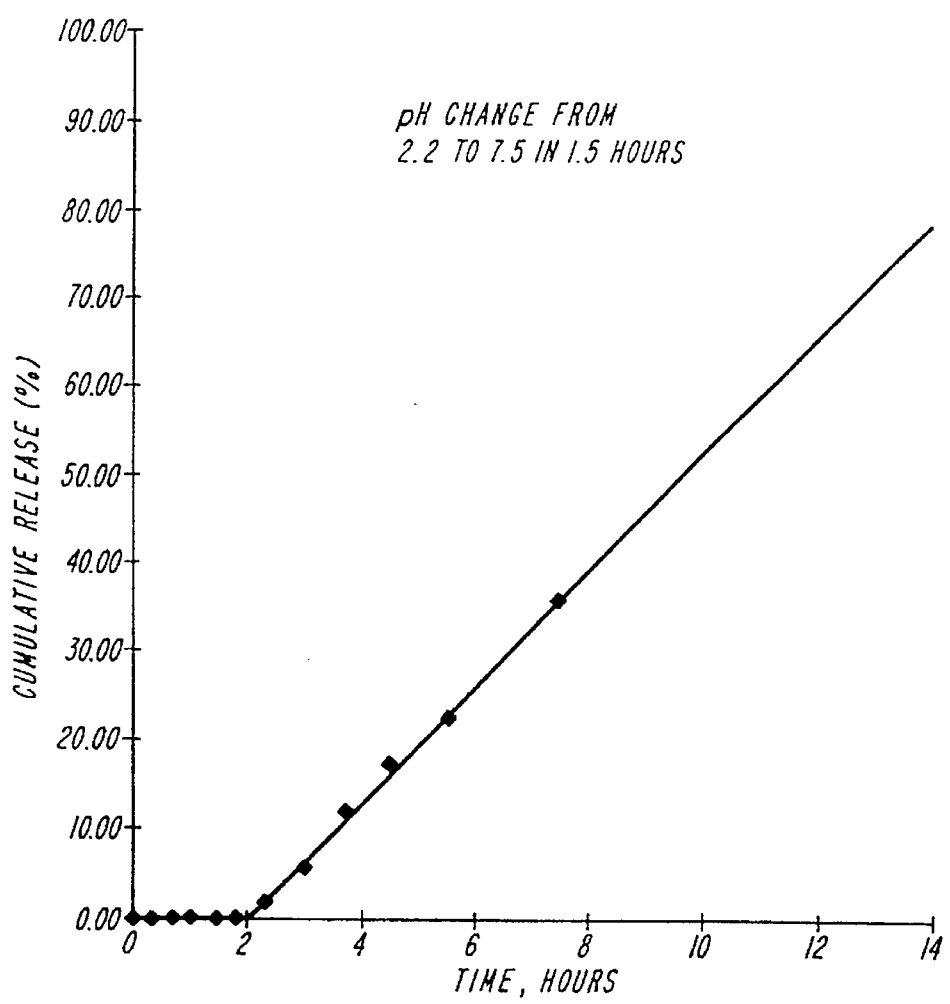
FIG. 2 is a graph of cumulative release versus time.
Figure 3:
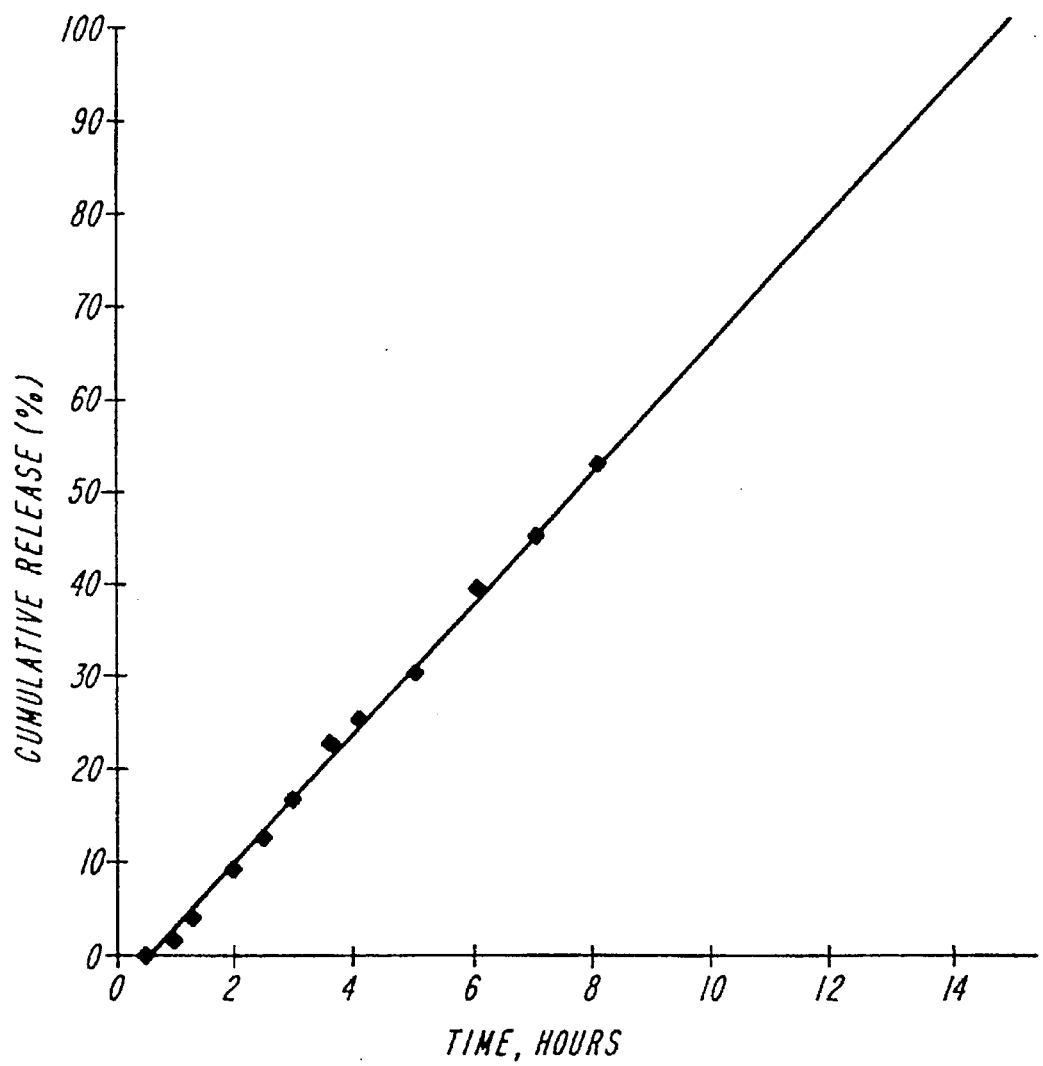
FIG. 3 is a graph of cumulative release versus time of a hydrophobic material into an aqueous environment.

With reference to FIG. 2, there is shown the cumulative release of a viscous hydrophilic material (0.5% Carbopol 934P, neutralized) measured at pH 2.2 (glycine buffer) for 1.5 hours, representing gastric residence time. The apparatus was then placed in a vessel containing Simulated Intestinal Fluid, USP (pH 7.5). This graph shows that there was no release of the material at low pH followed by release after the pH was raised to 7.5. In the experiment whose response is illustrated in FIG. 2, the hydrogel was hydroxypropylcellulose crosslinked with adipic acid. A gel having the response characteristics illustrated in FIG. 2 is suitable for a controlled release of a drug into the intestines. FIG. 3 illustrates the result of an experiment in which a hydrophobic material was released into an aqueous environment. A hydrophobic material, a mixture petrolatum and mineral oil, was placed into the experimental apparatus simulating the device in FIG. 1. The loaded system was then placed into a beaker containing a buffer. Cumulative release was measured by weighing the amount of petrolatum/mineral oil emitted from the apparatus and plotting the percent released over time. The hydrogel used to generate the expansion force to move the moveable partition was hydroxypropylcellulose crosslinked lightly with adipoyl chloride. This experiment demonstrates zero-order release of a hydrophobic material into a hydrophilic environment to complement the delivery of a hydrophilic material (FIG. 2) thereby indicating the ability of the apparatus of the present invention to deliver formulations irrespective of their physiochemical properties.

The hydrogel 22 in the compartment 12 is substantially independent of hydrostatic pressure as shown in the curves in FIG. 4. The material used in FIG. 4 is hydroxypropylcellulose (HPC) crosslinked with adipic acid.

In use, the device 10 would be placed into the mouth and swallowed. The pH of the mouth, esophagus and stomach are low so that no drug is released. When, however, the device 10 reaches the intestines, there will be encountered an environment having a higher pH. Communication with the higher pH environment through the screen or membrane 18 causes the hydrogel 22 to expand to move the partition 16 to expel the drug 24 into the intestinal region. It will be recognized and appreciated that following the teachings of this application and application Ser. No. 08/413,409, whose teachings are incorporated herein by reference, permit the design and engineering of hydrogels which undergo a volume change at a desired environmental condition or in a range of environmental conditions. In another embodiment, the gel in the device 10 may be triggered by a gradient in an ionic species in solution, for example, a potassium ion gradient. Such a trigger has application to drug delivery into the gastrointestinal tract.

Classes of biologically active compounds which can be loaded into the second compartment 14 include, but are not limited to, prodrugs, antisense, oligonucleotides, DNA, antibodies, vaccines, other recombinant proteins, anti-ADS substances, anti-cancer substances, antibiotics, immunosuppressants (e.g. cyclosporine) anti-viral substances, enzyme inhibitors, neurotoxins, opioids, hypnotics, antihistamines, lubricants tranquilizers, anti-convulsants, muscle relaxants and anti-Parkinson substances, anti-spasmodics and muscle contractants, miotics and anti-cholinergics, anti-glaucoma compounds, anti-parasite and/or ant-iprotozoal compounds, anti-hypertensives, analgesics, anti-pyretics and anti-inflammatory agents such as NSAIDs, local anesthetics, ophthalmics, prostaglandins, anti-depressants, anti-psychotic substances, anti-emetics, imaging agents, specific targeting agents, neurotransmitters, proteins, cell response modifiers, and vaccines.

Preferred crosslinked polymer networks for use in the device 10 of the invention are gels that are "responsive"—i.e., gels that, when challenged with an environmental condition, are affected by that environmental condition so as to cause the entire gel, or a component thereof, to undergo a reversible volumetric change in which the gel expands from a less liquid-filled state or a dry state to a more liquid-filled state; or collapses from a more liquid-filled state to a less liquid-filled state. The degree of volumetric change between collapsed and expanded states of preferred responsive gels at their particular environmental transition region is quantitatively much greater than the volume change of the gel outside the environmental transition region. Suitable gels for use in the present invention may be a single material such as a single polymer network which meets the volumetric response requirement. The gel may also be a copolymer, whether a random, alternating, or blocked co-polymer, that has a KATP and which meets the volumetric response requirement. The gel may also include two or more polymers, each component polymer having a KATP, so long as the result is a physical polymer blend, wherein at least one polymer meets the volumetric response requirement. The gel may also be an interpenetrating polymer network (IPN) in which each KATP polymer maintains its properties. The reversible volume change of the entire gel, or a component thereof, may be either continuous or discontinuous. A "continuous" volume change is marked by a reversible change in volume (i.e., a collapsed or swelling) that occurs over a relatively large change in environmental condition. There exists at least one stable volume near the transition between the swollen and collapsed states.

The crosslinked gels suitable for use in the invention may undergo a "discontinuous" volume change in which the reversible transition from swollen to collapsed states, and back again, occurs over a small change in environmental condition, such as less than $1/10°$ C. or $1/10$ pH unit. It is preferred that the discontinuous volume change occur within a range of approximately 5° C. and one pH unit. Such reversible gels are often called "phase-transition" gels (see, for example, Tanaka et al., *J. Chem. Phys.* 87(15), p.1392–4, 1987, which describes synthetic polymeric gels that undergo phase transitions). There is no stable volume between the swollen and collapsed states at the phase-transition and, in theory, the expansion and/or collapse occurs over an infinitesimally small environmental change. A gel undergoing a continuous phase-transition may have a similar order of magnitude total volume change as a gel undergoing a discontinuous phase-transition.

The volumetric changes of gels described herein result from competition between intermolecular forces, usually electrostatic in nature, that act to expand the polymer network; and at least one attractive force that acts to shrink it.

Volumetric changes in aqueous gels are driven primarily by four fundamental forces: ionic, hydrophobic, hydrogen bonding and van der Waals bonding interactions, either alone or in combination. Each of these interactions may be independently responsible for a volume transition in preferred gels of the invention. Each of these fundamental forces is most strongly affected by a particular trigger. Changes in solvent concentration most strongly affect the van der Waals interaction; changes in temperature most strongly affect hydrophobic interactions and hydrogen bonding; and changes in pH and ion concentration most strongly affect ionic interactions.

Thus, a gel whose volume change is governed by ionic interactions would include components that are weakly acidic and weakly basic, such as poly(methylmethacrylate)/dimethylaminoethyl methacrylate (see, for example, Siegel et al., *Macromolecules* 21(3254), 1988) and cellulose ethers such as HPC crosslinked by methods described herein. Gels of this type are sensitive to pH (see Example 1).

Gels whose volume change is governed by hydrogen bonding will collapse with a decrease in temperature and are exemplified by interpenetrating polymers that comprise acrylamide as one polymer, acrylic acid as the other polymer, and water as the liquid medium. Gels whose volume change is governed by hydrophobic interactions will collapse when challenged with an increase in temperature and are exemplified by N-isopropylacrylamide. Gels whose volume change is governed by van der Waals interactions will behave similarly to those governed by hydrophobic interactions.

Gels may be formulated in which the volume change is governed by more than one fundamental force. In particular, gels consisting of copolymers of positively and negatively charged groups meet this requirement. In these gels, polymer segments interact with each other through ionic interactions and hydrogen bonding. The combination of these forces results in the existence of several pH-driven phases (see, for example, Annaka et al., *Nature* 355(430), 1992, incorporated herein by reference). A fuller discussion is included in the above-referenced co-pending application.

Polymer gel compositions of the present invention are particularly useful for oral delivery compositions. It should also be noted that the device 10 could be located outside the body for other drug delivery applications such as cyclic infusions or transdermal delivery. For example, polymer gel networks of the present invention that are responsive to changes in pH or the other triggers discussed above can be utilized to effect controlled release of compounds at specific locations along the gastrointestinal tract. Similarly, polymer gel networks that are responsive to changes in pH can be utilized, for example, to effect controlled release of substances into only one of a cow's stomachs.

Without wishing to be bound by any theory, a cellulose ether gel such as hydroxypropylcellulose (HPC) with a lower critical solution temperature (LCST) near body temperature (e.g. 42° C.) should have its LCST shifted to a lower temperature at lower pH. This is because very few—COOH and/or —OH groups are ionized at low pH and the gel would tend to have a reduced hydrophilicity. At higher pH, many —COOH and/or —OH groups will be ionized and the LCST is shifted to a higher temperature due to increased hydrophilicity. Around body temperature, the gel is therefore very sensitive to pH change and would be collapsed at low pH (i.e. that of the stomach, where the drug would be retained in the device 10) and expanded at higher pH (i.e. that of the intestine, where the polymer gel network would expand and release the drug). A responsive gel may be made from starting materials (i.e. cellulose ethers of various configurations) that vary in their hydrophobic/hydrophilic nature when ionized, so that the methods described herein may be used to make a reversibly responsive, pH-sensitive gel with an LCST designed to match the body temperature of a desired subject. The LCST of preferred cellulose ethers is well known and can be easily determined and verified. Exemplary LCST's (°C.) are 49° (MEC); 42°–46° (HPC); 59° (methyl(hydroxypropyl)cellulose: HPMC); 60° methyl (hydroxyethyl)cellulose; and 55°–70° (ethyl(hydroxyethyl) cellulose).

The device 10 of the present invention provides better control of drug release than prior art, osmotic-type pump systems. The prior art devices release drugs solely as a function of time after ingestion rather than upon the encounter of an environmental condition such as pH. An example is U.S. Pat. No. 5,413,572 to Wong et al. which suggests the use of a hydrogel which expands upon contact with water whose expansion then disgorges a drug. While one or more of the hydrogels contemplated by Wong might exhibit a volume change in response to an environmental condition, this property is neither utilized nor appreciated by Wong et al. The Wong et al. hydrogels begin expanding upon contact with water immediately upon ingestion and thus the drug is continuously released. The hydrogels suitable for use in the device of the invention, on the other hand, expand only upon the achievement of a selected environmental condition such as a preselected narrow pH range or other disclosed triggers.

The following example teaches the preparation of a pH responsive gel suitable for use in the apparatus of the invention.

EXAMPLE 1:

Preparation of pH and Temperature Sensitive Hydroxypropylcellulose Gel With Adipoyl Chloride Reagent Exactly 50 mL of N-methyl pyrolidone (Fisher Scientific, Catalog No. 03688-4) was added to 5 grams of hydroxypropyl cellulose (Aqualon, Klucel 99-EF NF). The two materials were mixed on a magnetic stirrer for about 2 hours, while covered, to achieve a clear and colorless solution. This solution was then placed in a refrigerator for about 1 hour in order to achieve a solution temperature of 4°–8° C. To this solution, while stirring, 1 mL of cold (2°–8° C.) adipoyl chloride (Aldrich, Cat. No. 16,521-2) was added, and the resulting solution allowed to stir for 1 minute. After stirring, this solution was allowed to gel for eight hours.

A general protocol for forming a KATP polymer network suitable for use in the present invention using a crosslinkable polymer includes the steps of dissolving the KATP polymer (s) in a suitable solvent and allowing the polymer(s) and solvent to mix. A crosslinking agent is then added to the polymer solution, and the solution and crosslinker are further mixed together. The resulting solution may be poured into a solid mold (e.g. between two glass plates), and the crosslinking reaction carried out.

In an exemplary sequence, a chemical crosslinking reaction is carried out in the homogenous polymer state at room temperature to form a certain amount of polymer network.

Total crosslinking time will vary but is generally less than 24 hours. The network is then removed from its mold, and repeatedly washed to leach out any leachable material present in the network. In principle, a polymer network can be made from any KATP polymer with side groups that can react with a di- or multi-functional crosslinking molecule.

The polymer solution may also be formed into beads or spheres using crosslinking in a non-solid mold where the reacting solution (polymer, crosslinker and catalyst, if needed) is dispersed in a non-solvent to form a droplet. The solution reacts within the droplet to form a bead. In this method, the non-solvent may be considered to be a "mold" for polymer network droplets.

U.S. Pat. No. 3,208,994 to Flodin et al., incorporated herein by reference, generally discloses methods of preparing polysaccharide gel beads using suspension crosslinking. One introduces a water soluble polysaccharide and crosslinker into a suspension medium under agitation to obtain suspended drops of the polysaccharide solution. Another method of preparing gel beads uses inverse emulsion polymerization, in which a monomer solution is introduced into a dispersion solvent to form monomer droplets and polymerization is initiated to form polymer gel beads (see, for example, Hirose et al., *Macromolecules* 20(1342), 1987, incorporated herein by reference). Preferably, an aqueous cellulose ether solution, a non-polar saturated hydrocarbon solvent, and a crosslinker are provided and admixed to form a two-phase system. The two-phase system is agitated sufficiently to form droplets of aqueous cellulose ether solution in the two-phase system. The agitation of the two-phase system is maintained to form crosslinked cellulose ether gel beads and the crosslinked cellulose ether gel beads are thereafter recovered from the two-phase system.

Polymer networks of the invention also may consist, in whole or in part, of polymers made by copolymerization/ crosslinking of monofunctional and polyfunctional polymerizable monomers.

A preferred method for making KATP gels from cellulose ethers involves dissolving a sample of cellulose ether such as HPC or HPMC in an anhydrous solvent that does not contain active hydrogen, such as for example N-methyl pyrolidone (21 C.F.R. 176.300), dimethylsulfoxide (DMSO), dimethylformamide (DMF), methylethylketone (MEK), tetrahydrofuran (THF), and the like. The concentration of polymer in the solution may range from about 5–20% by weight of polymer per volume of solution, with a preferred concentration primarily a function of the kind of polymer used in the synthesis. The molecular weight of the cellulose ether should be at least about 20,000. Preferred molecular weights range from about 75,000 to about 150,000. The higher the molecular weight of the polymer, the sharper will be the volume change of the resulting responsive gel. This is because a higher molecular weight will result in formation of a more consistent three-dimensional polymer network. Molecular weights may range up to 1,000,000 or more although it will be understood that viscosity effects will place an upper limit on the molecular weight of the polymer starting material. Those having ordinary skill in the art may readily determine using the methods described herein the extent to which viscosity constraints interfere with the gel formation process and/or prevent the crosslinker from mixing with the polymer.

When synthesizing gels suitable for use with the invention with a crosslinker reagent that is a dicarboxylic acid, azeotropic distillation is a preferred method. A first solvent such as DMSO is added to a distillation flask containing the polymer and crosslinker reagents. Both are mixed to achieve a clear solution. To this solution, a small amount (several hundred µL) of an acidified solution of first solvent is added, followed by the addition of a second solvent (e.g. toluene). This solution is allowed to react under azeotropic distillation until a gel forms in the flask. The gel is then removed and placed in an excess of deionized water. The water is removed and excess primary alcohol (e.g. methanol) is added to remove excess solvent. The gel is washed and then dried in a desiccator.

Synthesis of KATP gels using acyl halide derivatives of dicarboxylic acids generally occurs as follows: While stirring the cellulose ether polymer solution under anhydrous conditions, the solution is cooled slightly below room temperature (in some embodiments to between about 10°–20° C.) and a cold solution (in some embodiments between about 2°–8° C.) of a preferred acyl halide derivative of a multifunctional carboxylic acid is added as crosslinker to the polymer solution. This solution is stirred and then allowed to sit until gelation has occurred. Gelation time will necessarily vary and may occur within about 2 hours (e.g. for HPC) or as long as 24 hours (e.g. for HPMC). The polymer/ crosslinker weight ratio is between about 12/1 and 8/1. The lower the ratio, the more highly crosslinked the resulting gel will be.

The reaction will not always produce polymer/ crosslinker/polymer covalent couplings, and a number of incomplete crosslinks will occur that will leave one end of the acid chloride group unreacted. After the crosslinking reaction, any unreacted acid chloride is quantitatively reacted with water to produce a carboxylic acid group. Carboxylic acid groups in the polymer network will provide a pH- and temperature- responsive gel (see Example 1).

Alternatively, if it is desired to produce a gel which has basic (amine) groups rather than acid groups, this may be achieved for example by allowing the acyl halide, cellulose ether reaction product to react with a KATP diamine such as ethylenediamine or hexamethylenediamine (21 C.F.R. 175.300 (b)(3) (xxxii) to produce an amine-terminated amide. The amine-terminated amide will survive the workup. These amine groups will cause the gel to be pH and temperature responsive in a range different from the acid group-containing gel.

After the gel is formed, destruction of any remaining acid chloride groups is carried out by soaking the gel in distilled water for about 12 hours. Solvent is then removed by soaking the gel in an alcohol (e.g. methanol, ethanol, and the like) for at least several hours so that the methanol can diffuse into the gel and the solvent can diffuse out of the gel. After several hours, the wash is drained off. This process is repeated at least 4–5 times. The gel is then washed 4–5 times with distilled water while it is being heated to between about 60°–80° C. for about 2 hours. Heating drives off any remaining alcohol, leaving gel and water. The process is repeated at least 3–5 times until the gel appears opaque at the elevated temperature. This opacity signifies that the gel has undergone a volumetric change at a lower critical solution temperature (LCST), and therefore that the gel has temperature responsive characteristics. For HPC, the LCST is between 42° and 46° C. The degree of responsiveness to pH may be assayed using the device and procedures given in Example 1.

Persons having ordinary skill in the art may readily determine if a particular KATP polymer material is capable of forming a polymer gel network by following the synthesis procedures described herein. Moreover, methods to determine the degree of crosslinking are conventional and are described, for example, by Peppas et al. (eds) in "Hydrogels in Medicine and Pharmacy" Vol. 1, CRC Press, Boca Raton, Fla., 1986. In operation, the first compartment 12 of the device 10 is loaded with a suitable hydrogel, as described above. A desired biologically active material or drug 24 is loaded into the second compartment 14. The thus loaded device is ingested and fluids in the environment pass through the screen or membrane 18 to interact with the hydrogel 22. When, for example, the pH is high (and only in that circumstance), the hydrogel 22 will undergo a volume expansion moving the moveable partition 16 to expel the drug 24 through the orifice 20. After drug 24 release, the device 10 will continue its passage through the system with subsequent natural elimination from the system.

It will be appreciated by those skilled in the art that other embodiments of the invention are within the scope of the claims. For example, responsive hydrogels may provide the motive force on the plunger of a syringe-like device to provide an external continuous IV/IM/SQ infusion. Similarly, such a device can be implemented within the body to provide controlled release of a suitable drug.

What is claimed is:

1. Apparatus for controlled delivery of a biologically active compound to a biological environment comprising:

first and second compartments separated by a moveable partition;

the first compartment including a screen or membrane forming at least a portion of a side of the first compartment, the first compartment containing a polymer gel network which undergoes a volume change in response to an environmental condition which varies in the biological environment;

the second compartment containing an effective amount of the biologically active compound and including an orifice communicating with the biological environment;

whereupon volume change of the polymer gel network moves the partition and causes the biologically active compound to be discharged into the biological environment through the orifice.

2. The apparatus of claim 1 wherein the environmental condition is pH.

3. The apparatus of claim 1 wherein the polymer gel network is in a collapsed state at low pH and in an expanded state had a high pH.

4. The apparatus of claim 1 wherein the polymer gel network has a known acceptable toxicological profile.

5. The apparatus of claim 1 wherein the crosslinked polymer gel network comprises a polymer selected from the group consisting of hydroxypropylcellulose, hydropropylmethylcellulose, starch, and hydroxyethylcellulose.

6. The apparatus of claim 1 wherein the environmental condition is selected from the group comprising: temperature, solvent composition, pH, electric field, magnetic field, light intensity, light wavelength, pressure, ionic strength, osmolarity, and electric current.

7. The apparatus of claim 1 wherein the polymer gel network is a responsive gel network.

8. The apparatus of claim 7 wherein the responsive gel network exhibits a continuous volume change.

9. The apparatus of claim 7 wherein the responsive gel network exhibits a discontinuous volume change.

10. Apparatus for controlled delivery of a composition comprising:

a compartment containing the composition; and a polymer gel adapted to undergo a volume change in response to a preselected physical condition; the volume change causing the composition to be expelled from the compartment.

11. Apparatus of claim 10 wherein the compartment is implanted into a body.

12. Apparatus of claim 10 wherein the compartment is external to the body.

* * * * *